(12) United States Patent
Jacobson et al.

(10) Patent No.: US 9,138,002 B2
(45) Date of Patent: *Sep. 22, 2015

(54) COMPOUNDS AND COMPOSITIONS

(71) Applicant: Dow AgroSciences LLC, Indianapolis, IN (US)

(72) Inventors: Richard Martin Jacobson, Chalfont, PA (US); Daniel Maclean, Woodland, CA (US); Esther Gachango, Davis, CA (US)

(73) Assignee: AgroFresh Inc., Collegeville, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/182,793

(22) Filed: Feb. 18, 2014

(65) Prior Publication Data

US 2014/0213551 A1  Jul. 31, 2014

Related U.S. Application Data

(62) Division of application No. 13/945,577, filed on Jul. 18, 2013, now Pat. No. 8,669,207.

(60) Provisional application No. 61/831,187, filed on Jun. 5, 2013, provisional application No. 61/758,313, filed on Jan. 30, 2013.

(51) Int. Cl.
*A01N 55/08* (2006.01)
*A61K 31/69* (2006.01)
*C07F 5/02* (2006.01)

(52) U.S. Cl.
CPC ............... *A01N 55/08* (2013.01); *A61K 31/69* (2013.01); *C07F 5/02* (2013.01)

(58) Field of Classification Search
CPC ........... A01N 55/08; A61K 31/69; C07F 5/02
USPC ............................................ 504/193; 514/64
See application file for complete search history.

(56) References Cited

U.S. PATENT DOCUMENTS

| | | | |
|---|---|---|---|
| 3,686,398 A | 8/1972 | Kohn et al. | |
| 3,873,279 A | 3/1975 | Singer | |
| 5,880,188 A | 3/1999 | Austin et al. | |
| 7,390,806 B2 | 6/2008 | Lee et al. | |
| 7,393,856 B2 | 7/2008 | Bellinger-Kawahara et al. | |
| 7,465,836 B2 | 12/2008 | Lee et al. | |
| 7,582,621 B2 | 9/2009 | Baker et al. | |
| 7,652,000 B2 | 1/2010 | Perry et al. | |
| 7,767,657 B2 | 8/2010 | Baker et al. | |
| 7,816,344 B2 | 10/2010 | Baker et al. | |
| 7,888,356 B2 | 2/2011 | Lee et al. | |
| 7,968,752 B2 | 6/2011 | Lee et al. | |
| 8,039,450 B2 | 10/2011 | Akama et al. | |
| 8,039,451 B2 | 10/2011 | Baker et al. | |
| 8,106,031 B2 | 1/2012 | Lee et al. | |
| 8,115,026 B2 | 2/2012 | Baker et al. | |
| 8,168,614 B2 | 5/2012 | Baker et al. | |
| 8,343,944 B2 | 1/2013 | Xia et al. | |
| 8,440,642 B2 | 5/2013 | Baker et al. | |
| 8,461,134 B2 | 6/2013 | Hernandez et al. | |
| 8,461,135 B2 | 6/2013 | Akama et al. | |
| 8,461,336 B2 | 6/2013 | Zhou et al. | |
| 8,461,364 B2 | 6/2013 | Wheeler et al. | |
| 8,470,803 B2 | 6/2013 | Akama et al. | |
| 8,501,712 B2 | 8/2013 | Baker et al. | |
| 8,546,357 B2 | 10/2013 | Akama et al. | |
| 8,669,207 B1 * | 3/2014 | Jacobson et al. ............... 504/193 |
| 2004/0259842 A1 | 12/2004 | Mikoshiba et al. | |
| 2007/0155699 A1 | 7/2007 | Baker et al. | |
| 2007/0293457 A1 | 12/2007 | Baker et al. | |
| 2008/0153992 A1 | 6/2008 | Knott et al. | |
| 2008/0293675 A1 | 11/2008 | Lee et al. | |
| 2008/0317737 A1 | 12/2008 | Patel et al. | |
| 2009/0227541 A1 | 9/2009 | Baker et al. | |
| 2009/0239824 A1 | 9/2009 | Lee et al. | |
| 2009/0291917 A1 | 11/2009 | Akama et al. | |
| 2010/0158992 A1 | 6/2010 | Black et al. | |
| 2010/0190748 A1 | 7/2010 | Baker et al. | |
| 2010/0256092 A1 | 10/2010 | Xia et al. | |
| 2010/0267981 A1 | 10/2010 | Baker et al. | |
| 2010/0292504 A1 | 11/2010 | Baker et al. | |

(Continued)

FOREIGN PATENT DOCUMENTS

| | | |
|---|---|---|
| AU | 2010203096 B2 | 2/2010 |
| AU | 2012327171 A1 | 6/2013 |
| AU | 2012327230 A1 | 7/2013 |
| CA | 2190155 A1 | 12/1995 |
| CN | 101505603 | 8/2009 |
| EP | 0765331 B1 | 9/2000 |
| EP | 1444981 A1 | 8/2004 |
| EP | 1980564 A1 | 10/2008 |
| EP | 1765360 B1 | 11/2009 |
| EP | 1765358 B1 | 2/2011 |
| EP | 2343304 A1 | 7/2011 |
| EP | 2564857 A1 | 3/2013 |
| GB | 961280 | 6/1964 |
| GB | 1006336 | 6/1965 |
| GB | 1396904 | 6/1975 |
| WO | 9533754 A1 | 12/1995 |
| WO | 2005087742 A1 | 9/2005 |
| WO | 2006089067 | 8/2006 |
| WO | 2006102604 | 9/2006 |
| WO | 2007071632 | 6/2007 |
| WO | 2007078340 A2 | 7/2007 |
| WO | 2007079119 A2 | 7/2007 |

(Continued)

OTHER PUBLICATIONS

Alexander et al., "Imprinted Polymers as Protecting Groups for Regioselective Modification of Polyfunctional Substrates", Journal of American Chemical Society, 1999, pp. 6640-6651, vol. 121, United Kingdom (12 pages).

(Continued)

*Primary Examiner* — Golam M M Shameem
(74) *Attorney, Agent, or Firm* — Taft Stettinius & Hollister, LLP; Gregory B. Coy

(57) ABSTRACT

This invention is related to compounds and/or compositions useful against pathogens affecting meats, plants, or plant parts. In one embodiment, the provided compounds are products of certain oxaborole moieties. In a further embodiment, the compound comprises a di-oxaborole compound. Delivery systems are also provided to take advantage of the volatile nature of these compounds and/or compositions.

14 Claims, No Drawings

(56) References Cited

U.S. PATENT DOCUMENTS

| | | |
|---|---|---|
| 2011/0059985 A1 | 3/2011 | Schmidts et al. |
| 2011/0076261 A1 | 3/2011 | Patel et al. |
| 2011/0082118 A1 | 4/2011 | Patel et al. |
| 2011/0124597 A1 | 5/2011 | Hernandez et al. |
| 2011/0136763 A1 | 6/2011 | Xia et al. |
| 2011/0152217 A1 | 6/2011 | Wheeler et al. |
| 2011/0166103 A1 | 7/2011 | Akama et al. |
| 2011/0166104 A1 | 7/2011 | Zhou et al. |
| 2011/0172187 A1 | 7/2011 | Hernandez et al. |
| 2011/0190235 A1 | 8/2011 | Chen et al. |
| 2011/0207701 A1 | 8/2011 | Zhou et al. |
| 2011/0207702 A1 | 8/2011 | Jacobs et al. |
| 2011/0212918 A1 | 9/2011 | Hernandez et al. |
| 2011/0319361 A1 | 12/2011 | Baker et al. |
| 2012/0035132 A1 | 2/2012 | Jarnagin et al. |
| 2012/0115813 A1 | 5/2012 | Hernandez et al. |
| 2012/0214765 A1 | 8/2012 | Akama et al. |
| 2012/0264714 A1 | 10/2012 | Baker et al. |
| 2012/0289686 A1 | 11/2012 | Baker et al. |
| 2012/0295875 A1 | 11/2012 | Zhou et al. |
| 2013/0059802 A1 | 3/2013 | Baker et al. |
| 2013/0059803 A1 | 3/2013 | Baker et al. |
| 2013/0064783 A1 | 3/2013 | Baker et al. |
| 2013/0131016 A1 | 5/2013 | Akama et al. |
| 2013/0131017 A1 | 5/2013 | Akama et al. |
| 2013/0196433 A1 | 8/2013 | Raines et al. |
| 2013/0210770 A1 | 8/2013 | Baker et al. |
| 2013/0231304 A1 | 9/2013 | Jacobs et al. |
| 2013/0244980 A1 | 9/2013 | Baker et al. |
| 2013/0316979 A1 | 11/2013 | Baker et al. |

FOREIGN PATENT DOCUMENTS

| | | |
|---|---|---|
| WO | 2007095638 A2 | 8/2007 |
| WO | 2007131072 A2 | 11/2007 |
| WO | 2007146965 A2 | 12/2007 |
| WO | 2008064345 A2 | 5/2008 |
| WO | 2008070257 A2 | 6/2008 |
| WO | 2008115385 A2 | 9/2008 |
| WO | 2008156798 A1 | 12/2008 |
| WO | 2008157726 A1 | 12/2008 |
| WO | 2009046098 A1 | 4/2009 |
| WO | 2009053741 A2 | 4/2009 |
| WO | 2009111676 A2 | 9/2009 |
| WO | 2009140309 A2 | 11/2009 |
| WO | 2010027975 A1 | 3/2010 |
| WO | 2010028005 A1 | 3/2010 |
| WO | 2010045503 A1 | 4/2010 |
| WO | 2010045505 A1 | 4/2010 |
| WO | 2010080558 A1 | 7/2010 |
| WO | 2010136475 A1 | 12/2010 |
| WO | 2011017125 A1 | 2/2011 |
| WO | 2011019612 A1 | 2/2011 |
| WO | 2011019616 A1 | 2/2011 |
| WO | 2011019618 A1 | 2/2011 |
| WO | 2011022337 A1 | 2/2011 |
| WO | 2011037731 A1 | 3/2011 |
| WO | 2011049971 A1 | 4/2011 |
| WO | 2011060196 A1 | 5/2011 |
| WO | 2011060199 A1 | 5/2011 |
| WO | 2011063293 A1 | 5/2011 |
| WO | 2011094450 A1 | 8/2011 |
| WO | 2011116348 A1 | 9/2011 |
| WO | 2011150190 A2 | 12/2011 |
| WO | 2012033858 A2 | 3/2012 |
| WO | 2012067663 A1 | 5/2012 |
| WO | 2012069652 A2 | 5/2012 |
| WO | 2012139134 A2 | 10/2012 |
| WO | 2012154213 A1 | 11/2012 |
| WO | 2013033270 A2 | 3/2013 |
| WO | 2013050591 A2 | 4/2013 |
| WO | 2013057740 A2 | 4/2013 |
| WO | 2013058824 A1 | 4/2013 |
| WO | 2013078070 A1 | 5/2013 |
| WO | 2013078071 A1 | 5/2013 |
| WO | 2013108024 A1 | 7/2013 |
| WO | 2013110005 A1 | 7/2013 |
| WO | 2013154759 A1 | 10/2013 |

OTHER PUBLICATIONS

Haynes et al., "Reactions of Boronophthalide", Noyes Chemical Laboratory, University of Illinois, Nov. 1964, pp. 3233, Urbana, USA (5 pages).

Kumar et al., "Development of Practical Methodologies for the Synthesis of Functionalized Benzoboroxoles", Tetrahendron Letters, Elsevier, Amsterdam, NL, col. 51, No. 34, Aug. 25, 2010, pp. 4482-4485.

* cited by examiner

COMPOUNDS AND COMPOSITIONS

CROSS REFERENCE TO RELATED APPLICATIONS

This application is a divisional of U.S. patent application Ser. No. 13/945,577 filed Jul. 18, 2013, which claims the benefit of U.S. Provisional Application No. 61/831,187 filed Jun. 5, 2013, and U.S. Provisional Application No. 61/758,313 filed Jan. 30, 2013, the disclosures of which are incorporated herein by reference in their entirety.

BACKGROUND OF THE INVENTION

A number of compounds containing an oxaborole ring have been disclosed previously. However, there has been no teaching that these oxaborole compounds are volatile antimicrobial agents. In addition, there has been no teaching for adducting or conjugating these oxaborole compounds while maintaining their antimicrobial activity and/or volatility.

Thus, there remains a need to develop new use of various volatile antimicrobial agents, and/or combination with a volatile plant growth regulator, in particular for agricultural applications.

SUMMARY OF THE INVENTION

This invention is related to compounds and/or compositions useful against pathogens affecting meats, plants, or plant parts. In one embodiment, the provided compounds are products of certain oxaborole moieties. In a further embodiment, the compound comprises a di-oxaborole compound. Delivery systems are also provided to take advantage of the volatile nature of these compounds and/or compositions.

In one aspect, provided is a compound having a structure of formula (A):

wherein
each of $R^A$ and $R^B$ is independently derived from a member selected from the group consisting of 5-fluoro-1,3-dihydro-1-hydroxy-2,1-benzoxaborole; 5-chloro-1,3-dihydro-1-hydroxy-2,1-benzoxaborole; 1,3-dihydro-1-hydroxy-2,1-benzoxaborole; and combinations thereof;
the -$L^A$-G-$L^B$- portion of formula (A) is derived from a diol or diamine compound; the diol compound is selected from the group consisting of 1,2-ethylene glycol; 1,2-propylene glycol; 1,3-propylene glycol; 1,1,2,2-tetramethyl-1,2-ethylene glycol; 2,2-dimethyl-1,3-propylene glycol; 1,6-hexanediol; 1,10-decanediol; and combinations thereof; and the diamine compound is 1,2-ethylene diamine; 1,3-propylene diamine; or combinations thereof;
G is a substituted or unsubstituted $C_{1-8}$-alkylene;
and agriculturally acceptable salts thereof.

In one embodiment, the compound comprises a di-oxaborole compound. In another embodiment, the compound is volatile. In another embodiment, the compound has antimicrobial activity. In another embodiment, the compound has use against pathogens affecting meats, plants, or plant parts. In a further embodiment, the compound is a fungicide. In another embodiment, G is selected from —$CH_2$—, —$CH_2$—$CH_2$—, —$CH_2$—$CH_2$—$CH_2$—, —$CH(CH_3)$—$CH_2$—, —$C(CH_3)_2$—$C(CH_3)_2$—, and —$CH_2$—$C(CH_3)_2$—$CH_2$—. In another embodiment, G is selected from —$CH_2$—, —$CH_2$—$CH_2$—, and —$CH_2$—$CH_2$—$CH_2$—.

In another embodiment, each of $R^A$ and $R^B$ is independently

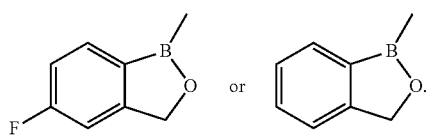

In another embodiment, the compound has the structure of

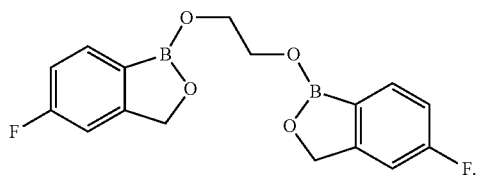 [SMILES: Fc1ccc2c(c1)COB2OCCOB1OCc2cc(F)ccc21]

In another aspect, provided is a mixture or composition comprising the compound described herein.

In another aspect, provided is a method of using a compound against pathogens affecting meats, plants, or plant parts. The method comprises contacting the meats, plants, or plant parts with an effective amount of the compound having a structure of formula (A):

wherein
each of $R^A$ and $R^B$ is independently derived from a member selected from the group consisting of 5-fluoro-1,3-dihydro-1-hydroxy-2,1-benzoxaborole; 5-chloro-1,3-dihydro-1-hydroxy-2,1-benzoxaborole; 1,3-dihydro-1-hydroxy-2,1-benzoxaborole; and combinations thereof;
the -$L^A$-G-$L^B$- portion of formula (A) is derived from a diol or diamine compound; the diol compound is selected from the group consisting of 1,2-ethylene glycol; 1,2-propylene glycol; 1,3-propylene glycol; 1,1,2,2-tetramethyl-1,2-ethylene glycol; 2,2-dimethyl-1,3-propylene glycol; 1,6-hexanediol; 1,10-decanediol; and combinations thereof; and the diamine compound is 1,2-ethylene diamine; 1,3-propylene diamine; or combinations thereof;
G is a substituted or unsubstituted $C_{1-8}$-alkylene;
and agriculturally acceptable salts thereof.

In one embodiment, the compound is volatile. In another embodiment, the compound is a fungicide. In another embodiment, G is selected from —$CH_2$—, —$CH_2$—$CH_2$—, —$CH_2$—$CH_2$—$CH_2$—, —$CH(CH_3)$—$CH_2$—, —$C(CH_3)_2$—$C(CH_3)_2$—, and —$CH_2$—$C(CH_3)_2$—$CH_2$—. In another embodiment, G is selected from —$CH_2$—, —$CH_2$—$CH_2$—, and —$CH_2$—$CH_2$—$CH_2$—.

In another embodiment, each of $R^A$ and $R^B$ is independently

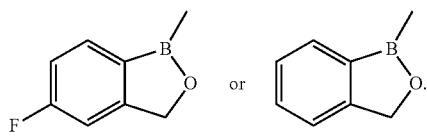

In another embodiment, the compound has the structure of

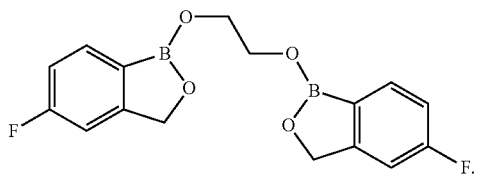 [SMILES: Fc1ccc2c(c1)COB2OCCOB1OCc2cc(F)ccc21]

In one embodiment of the method provided, the pathogen comprises fungi. In another embodiment, the pathogen is selected from the group consisting of *Acremonium* spp., *Albugo* spp., *Alternaria* spp., *Ascochyta* spp., *Aspergillus* spp., *Botryodiplodia* spp., *Botryospheria* spp., *Botrytis* spp., *Byssochlamys* spp., *Candida* spp., *Cephalosporium* spp., *Ceratocystis* spp., *Cercospora* spp., *Chalara* spp., *Cladosporium* spp., *Colletotrichum* spp., *Cryptosporiopsis* spp., *Cylindrocarpon* spp., *Debaryomyces* spp., *Diaporthe* spp., *Didymella* spp., *Diplodia* spp., *Dothiorella* spp., *Elsinoe* spp., *Fusarium* spp., *Geotrichum* spp., *Gloeosporium* spp., *Glomerella* spp., *Helminthosporium* spp., *Khuskia* spp., *Lasiodiplodia* spp., *Macrophoma* spp., *Macrophomina* spp., *Microdochium* spp., *Monilinia* spp., *Monilochaethes* spp., *Mucor* spp., *Mycocentrospora* spp., *Mycosphaerella* spp., *Nectria* spp., *Neofabraea* spp., *Nigrospora* spp., *Penicillium* spp., *Peronophythora* spp., *Peronospora* spp., *Pestalotiopsis* spp., *Pezicula* spp., *Phacidiopycnis* spp., *Phoma* spp., *Phomopsis* spp., *Phyllosticta* spp., *Phytophthora* spp., *Polyscytalum* spp., *Pseudocercospora* spp., *Pyricularia* spp., *Pythium* spp., *Rhizoctonia* spp., *Rhizopus* spp., *Sclerotium* spp., *Sclerotinia* spp., *Septoria* spp., *Sphaceloma* spp., *Sphaeropsis* spp., *Stemphyllium* spp., *Stilbella* spp., *Thielaviopsis* spp., *Thyronectria* spp., *Trachysphaera* spp., *Uromyces* spp., *Ustilago* spp., *Venturia* spp., and *Verticillium* spp. In another embodiment, the pathogen is selected from the group consisting of *Alternaria* spp., *Aspergillus* spp., *Botryospheria* spp., *Botrytis* spp., *Byssochlamys* spp., *Colletotrichum* spp., *Diplodia* spp., *Fusarium* spp., *Geotrichum* spp., *Lasiodiplodia* spp., *Monilinia* spp., *Mucor* spp., *Penicillium* spp., *Pezicula* spp., *Phomopsis* spp., *Phytophthora* spp., *Pythium* spp., *Rhizoctonia* spp., *Rhizopus* spp., *Sclerotinia* spp., and *Venturia* spp.

In another embodiment, the pathogen comprises bacteria. In another embodiment, the pathogen is selected from the group consisting of *Bacillus* spp., *Campylobacter* spp., *Clavibacter* spp., *Clostridium* spp., *Erwinia* spp., *Escherichia* spp., *Lactobacillus* spp., *Leuconostoc* spp., *Listeria* spp., *Pantoea* spp., *Pectobacterium* spp., *Pseudomonas* spp., *Ralstonia* spp., *Salmonella* spp., *Shigella* spp., *Staphylococcus* spp., *Vibrio* spp., *Xanthomonas* spp., and *Yersinia* spp. In another embodiment, the pathogen is selected from the group consisting of *Cryptosporidium* spp. and *Giardia* spp.

In another embodiment, the method comprises a pre-harvest treatment or post-harvest treatment. In a further embodiment, the pre-harvest treatment is selected from the group consisting of seed treatment and transplant treatment. In another embodiment, the post-harvest treatment is selected from the group consisting of treatment during field packing, treatment during grading and sorting, treatment during palletization, in-box treatment, in-packaging treatment (e.g., in clamshell or similar), treatment during transportation (in transport trailer, marine container, airplane cargo, train car, or similar), and treatment during storage and/or throughout distribution network.

In another embodiment, the post-harvest treatment is performed in an enclosure. In a further embodiment, the enclosure is selected from the group consisting of a package, a box, a wrapped pallet, a sea container, a building, a room, and combinations thereof.

In another embodiment, the plants or plant parts comprise transgenic plants or transgenic plant parts. In another embodiment, the plants or plant parts are selected from the group consisting of barley, canola, coffee, corn, cotton, flax, grapevine, hops, mustard, nuts, oat, poppy, rape, rice, rubber plant, rye, sunflower, sorghum, soybean, sugar cane, tea, tobacco, and wheat. In another embodiment, the plants or plant parts are selected from the group consisting of corn, wheat, cotton, rice, soybean, and canola. In another embodiment, the plants are selected from the group consisting of banana, pineapple, citrus, grapes, watermelon, cantaloupe, muskmelon, and other melons, apple, peach, pear, cherry, kiwifruit, mango, nectarine, guava, papaya, persimmon, pomegranate, avocado, fig, citrus, and berries.

In another embodiment, the plants or plant parts are selected from the group consisting of flowers, fruit, vegetables, nursery, turf and ornamental crops. In a further embodiment, the fruit is selected from the group consisting of almond, apple, avocado, banana, berries (including strawberry, blueberry, raspberry, blackberry, currents and other types of berries), carambola, cherry, citrus (including oranges, lemon, lime, mandarin, grapefruit, and other citrus), coconut, fig, grapes, guava, kiwifruit, mango, nectarine, melons (including cantaloupe, muskmelon, watermelon, and other melons), olive, papaya, passionfruit, peach, pear, persimmon, pineapple, plum, and pomegranate. In a further embodiment, the vegetable is selected from the group consisting of asparagus, beet (for example sugar beet and fodder beet), beans, broccoli, cabbage, carrot, cassava, cauliflower, celery, cucumber, eggplant, garlic, gherkin, leafy greens (lettuce, kale, spinach, and other leafy greens), leek, lentils, mushroom, onion, peas, pepper (for example sweet pepper, bell pepper, and hot pepper), potato, pumpkin, sweet potato, snap bean, squash, and tomato. In another embodiment, the nursery plant or flower or flower part is selected from the group consisting of baby's breath, carnation, dahlia, daffodil, geranium, gerbera, lily, orchid, peony, Queen Anne's lace, rose, snapdragon, or other cut-flowers or ornamental flowers, potted flowers, flower bulbs, shrub, deciduous or coniferous tree. In a further embodiment, the meat is selected from the group of beef, bison, chicken, deer, goat, turkey, pork, sheep, fish, shellfish, mollusks, or dry-cured meat products.

In one embodiment, the contacting comprises applying the compound by ways selected from the group consisting of spray, mist, thermal or non-thermal fogging, drench, gas treatment, incorporation into a wax coating, and combinations thereof. In a further embodiment, the gas treatment is selected from the group consisting of release from a sachet, release from a synthetic or natural film, fibrous material, and/or release from liner or other packaging materials, release from powder, release from a gas-releasing generator, release using a compressed or non-compressed gas cylinder, release from a droplet inside a box, wax coating, and combinations thereof.

In another aspect, provided is a method of preparing a compound. The method comprises:
(a) mixing at least one oxaborole compound with at least one adducting compound in a first organic solvent; and
(b) evaporating the first organic solvent by heating, thereby allowing the at least one adducting compound to react with the at least one oxaborole compound to generate at least one adducted product.

In another embodiment, the heating is performed at a temperature between 110° C. and 125° C.; between 100° C. and 150° C.; or between 80° C. and 200° C.

In another embodiment, the at least one adducting compound comprises a diol or diamine compound. In a further embodiment, the diol compound is selected from the group consisting of 1,2-ethylene glycol; 1,2-propylene glycol; 1,3-propylene glycol; 1,1,2,2-tetramethyl-1,2-ethylene glycol; 2,2-dimethyl-1,3-propylene glycol; 1,6-hexanediol; 1,10-decanediol; and combinations thereof. In another embodiment, the diamine compound is 1,2-ethylene diamine; 1,3-propylene diamine; or combinations thereof.

In another embodiment, the at least one oxaborole compound comprises a compound selected from the group consisting of 5-fluoro-1,3-dihydro-1-hydroxy-2,1-benzoxaborole; 5-chloro-1,3-dihydro-1-hydroxy-2,1-benzoxaborole; 1,3-dihydro-1-hydroxy-2,1-benzoxaborole; and combinations thereof.

In another embodiment, the at least one oxaborole compound comprises a compound of a structure selected from

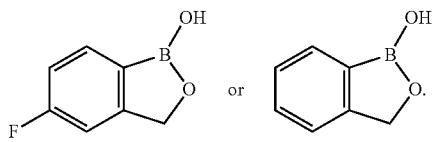 [SMILES: OB1OCc2cc(F)ccc21 ; OB1OCc2ccccc21]

In another embodiment, the at least one oxaborole compound comprises a compound having a structure of

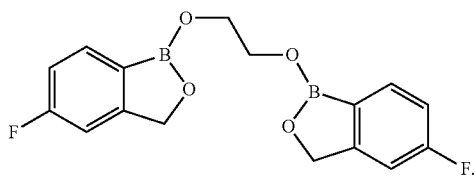 [SMILES: Fc1ccc2c(c1)COB2OCCOB1OCc2cc(F)ccc21]

DETAILED DESCRIPTION OF THE INVENTION

This invention is based on surprising results that the two to one adduct of oxaborole compounds with diols and/or diamines (or alternatively asymmetrical bridges for example amino alcohol) can (1) possess volatile properties at room temperature; and (2) have antimicrobial activity against for example fungi, especially *Botrytis cinerea*. One example includes the two to one adduct of 5-fluoro-1-hydroxy-2,1-benzoxaborole with ethylene glycol, which shows excellent activity against *Botrytis cinerea*. Volatile antimicrobial agents (for example fungicides) have utility in postharvest disease control. Provided are methods using reaction of certain 1-hydroxybenzoxaborole compounds with certain diol compounds to form compounds having antimicrobial activity, and compounds and/or composition prepared by the methods disclosed.

Unless otherwise stated, the following terms used in this application, including the specification and claims, have the definitions given below. It must be noted that, as used in the specification and the appended claims, the singular forms "a," "an," and "the" include plural referents unless the context clearly dictates otherwise. The definition of standard chemistry terms may be found in reference works, including Carey and Sundberg, *Advanced Organic Chemistry* 4$^{th}$ Ed., Vols. A (2000) and B (2001), Plenum Press, New York, N.Y.

As used herein, the phrase "moiety" refers to a specific segment or functional group of a molecule. Chemical moieties are often recognized chemical entities embedded in or appended to a molecule.

As used herein, the phrases "heteroatom" and "hetero-" refer to atoms other than carbon (C) and hydrogen (H). Examples of heteroatoms include oxygen (O), nitrogen (N) sulfur (S), silicon (Si), germanium (Ge), aluminum (Al) and boron (B).

As used herein, the phrases "halo" and "halogen" are interchangeable and refer to fluoro (—F), chloro (—Cl), bromo (—Br), and iodo (—I).

As used herein, the phrase "alkyl" refers to an unsubstituted or substituted, hydrocarbon group and can include straight, branched, cyclic, saturated and/or unsaturated features. Although the alkyl moiety may be an "unsaturated alkyl" moiety, which means that it contains at least one alkene or alkyne moiety, typically, the alkyl moiety is a "saturated alkyl" group, which means that it does not contain any alkene or alkyne moieties. Likewise, although the alkyl moiety may be a cyclic, typically the alkyl moiety is a non-cyclic group. Thus, in some embodiments, "alkyl" refers to an optionally substituted straight-chain, or optionally substituted branched-chain saturated hydrocarbon monoradical having from about one to about thirty carbon atoms in some embodiments, from about one to about fifteen carbon atoms in some embodiments, and from about one to about six carbon atoms in further embodiments. Examples of saturated alkyl radicals include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, sec-butyl, t-butyl, n-pentyl, isopentyl, neopentyl, and n-hexyl, and longer alkyl groups, such as heptyl, and octyl. It should be noted that whenever it appears herein, a numerical range such as "1 to 6" refers to each integer in the given range; e.g., "1 to 6 carbon atoms" or "$C_{1-6}$" or "$C_1$-$C_6$" means that the alkyl group may consist of 1 carbon atom, 2 carbon atoms, 3 carbon atoms, 4 carbon atoms, 5 carbon atoms, and/or 6 carbon atoms, although the present definition also covers the occurrence of the term "alkyl" where no numerical range is designated.

As used herein, the phrase "substituted alkyl" refers to an alkyl group, as defined herein, in which one or more (up to about five, preferably up to about three) hydrogen atoms is replaced by a substituent independently selected from the substituent group defined herein.

As used herein, the phrases "substituents" and "substituted" refer to groups which may be used to replace another group on a molecule. Such groups are known to those of skill in the chemical arts and may include, without limitation, one or more of the following independently selected groups, or designated subsets thereof: halogen, —CN, —OH, —NO$_2$, —N$_3$, =O, =S, =NH, —SO$_2$, —NH$_2$, —COOH, nitroalkyl, amino, including mono- and di-substituted amino groups, cyanato, isocyanato, thiocyanato, isothiocyanato, guanidinyl, O-carbamyl, N-carbamyl, thiocarbamyl, uryl, isouryl, thiouryl, isothiouryl, mercapto, sulfanyl, sulfinyl, sulfonyl, sulfonamidyl, phosphonyl, phosphatidyl, phosphoramidyl, dialkylamino, diarylamino, diarylalkylamino; and the protected compounds thereof. The protecting groups that may form the protected compounds of the above substituents are known to those of skill in the art and may be found in references such as Greene and Wuts, Protective Groups in Organic Synthesis, 3d Ed., John Wiley & Sons, New York, N.Y. (1999) and Kocienski, Protective Groups, Thieme Verlag, New York, N.Y. (1994) which are incorporated herein by reference in their entirety.

As used herein, the phrase "alkoxy" refers to the group —O-alkyl, where alkyl is as defined herein. In one embodiment, alkoxy groups include, e.g., methoxy, ethoxy, n-propoxy, iso-propoxy, n-butoxy, tert-butoxy, sec-butoxy, n-pentoxy, n-hexoxy, 1,2-dimethylbutoxy, and the like. The alkoxy can be unsubstituted or substituted.

As used herein, the phrases "cyclic" and "membered ring" refer to any cyclic structure, including alicyclic, heterocyclic, aromatic, heteroaromatic and polycyclic fused or non-fused ring systems as described herein. The term "membered" is meant to denote the number of skeletal atoms that constitute the ring. Thus, for example, pyridine, pyran, and pyrimidine are six-membered rings and pyrrole, tetrahydrofuran, and thiophene are five-membered rings.

As used herein, the phrase "aromatic" refers to a cyclic or polycyclic moiety having a conjugated unsaturated (4n+2) π electron system (where n is a positive integer), sometimes referred to as a delocalized π electron system.

As used herein, the phrase "aryl" refers to an optionally substituted, aromatic, cyclic, hydrocarbon monoradical of from six to about twenty ring atoms, preferably from six to about ten carbon atoms and includes fused (or condensed) and non-fused aromatic rings. A fused aromatic ring radical contains from two to four fused rings where the ring of attachment is an aromatic ring, and the other individual rings within the fused ring may be cycloalkyl, cycloalkenyl, cycloalkynyl, heterocycloalkyl, heterocycloalkenyl, heterocycloalkynyl, aromatic, heteroaromatic or any combination thereof. A non-limiting example of a single ring aryl group includes phenyl; a fused ring aryl group includes naphthyl, anthryl, azulenyl; and a non-fused bi-aryl group includes biphenyl.

As used herein, the phrase "substituted aryl" refers to an aryl group, as defined herein, in which one or more (up to about five, preferably up to about three) hydrogen atoms is replaced by a substituent independently selected from the group defined herein, (except as otherwise constrained by the definition for the aryl substituent).

As used herein, the phrase "heteroaryl" refers to an optionally substituted, aromatic, cyclic monoradical containing from about five to about twenty skeletal ring atoms, preferably from five to about ten ring atoms and includes fused (or condensed) and non-fused aromatic rings, and which have one or more (one to ten, preferably about one to about four) ring atoms selected from an atom other than carbon (i.e., a heteroatom) such as, for example, oxygen, nitrogen, sulfur, selenium, phosphorus or combinations thereof. The term heteroaryl includes optionally substituted fused and non-fused heteroaryl radicals having at least one heteroatom. A fused heteroaryl radical may contain from two to four fused rings where the ring of attachment is a heteroaromatic ring and the other individual rings within the fused ring system may be alicyclic, heterocyclic, aromatic, heteroaromatic or any combination thereof. The term heteroaryl also includes fused and non-fused heteroaryls having from five to about twelve skeletal ring atoms, as well as those having from five to about ten skeletal ring atoms. Examples of heteroaryl groups include, but are not limited to, acridinyl, benzo[1,3]dioxole, benzimidazolyl, benzindazolyl, benzoisooxazolyl, benzokisazolyl, benzofuranyl, benzofurazanyl, benzopyranyl, benzothiadiazolyl, benzothiazolyl, benzo[b]thienyl, benzothiophenyl, benzothiopyranyl, benzotriazolyl, benzoxazolyl, carbazolyl, carbolinyl, chromenyl, cinnolinyl, furanyl, furazanyl, furopyridinyl, furyl, imidazolyl, indazolyl, indolyl, indolidinyl, indolizinyl, isobenzofuranyl, isoindolyl, isoxazolyl, isoquinolinyl, isothiazolyl, naphthylidinyl, naphthyridinyl, oxadiazolyl, oxazolyl, phenoxazinyl, phenothiazinyl, phenazinyl, phenoxathiynyl, thianthrenyl, phenathridinyl, phenathrolinyl, phthalazinyl, pteridinyl, purinyl, puteridinyl, pyrazyl, pyrazolyl, pyridyl, pyridinyl, pyridazinyl, pyrazinyl, pyrimidinyl, pyrimidyl, pyrrolyl, quinazolinyl, quinolinyl, quinoxalinyl, tetrazolyl, thiadiazolyl, thiazolyl, thienyl, triazinyl, (1,2,3,)- and (1,2,4)-triazolyl and the like, and their oxides where appropriate, such as for example pyridyl-N-oxide.

As used herein, the phrase "substituted heteroaryl" refers to a heteroaryl group, as defined herein, in which one or more (up to about five, preferably up to about three) hydrogen atoms is replaced by a substituent independently selected from the group defined herein.

As used herein, the phrase "leaving group" refers to a group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like. In some embodiments, a leaving group can be HC(O)—COOH or RC(O)—COOH, wherein R is a $C_1$-$C_6$ alkyl or substituted $C_1$-$C_6$ alkyl.

As used herein, the phrase "derived from" in a statement that an $R^A$ or $R^B$ moiety or a -$L^A$-G-$L^B$- portion of formula (A) is derived from a certain precursor compound is understood by a person of ordinary skill in the art to indicate that the identified moiety or portion is one that can become part of formula (A) by reaction of the identified precursor compound with another precursor compound, whereby the identified $R^A$ or $R^B$ moiety or -$L^A$-G-$L^B$- portion retains all or substantially all of the structure of the precursor compound. "Substantially all" in the preceding sentence is understood to include the entire structure of the precursor compound except for one or more hydrogen, one or more hydroxide, or combinations thereof.

The compounds of the invention as described herein may be synthesized using standard synthetic techniques known to those of skill in the art or using methods known in the art in combination with methods described herein. The starting materials used for the synthesis of the compounds of the invention as described herein, can be obtained from commercial sources, such as Aldrich Chemical Co. (Milwaukee, Wis.), Sigma Chemical Co. (St. Louis, Mo.), or the starting materials can be synthesized. The compounds described herein, and other related compounds having different substituents can be synthesized using techniques and materials known to those of skill in the art, such as described, for example, in March, *Advanced Organic Chemistry* 4$^{th}$ Ed. (1992) John Wiley & Sons, New York, N.Y.; Carey and Sundberg, *Advanced Organic Chemistry* 4$^{th}$ Ed., Vols. A (2000) and B (2001) Plenum Press, New York, N.Y. and Greene and Wuts, *Protective Groups in Organic Synthesis,* 3rd Ed. (1999) John Wiley & Sons, New York, N.Y., (all of which are incorporated by reference in their entirety). General methods for the preparation of compound as disclosed herein may be derived from known reactions in the field, and the reactions may be modified by the use of appropriate reagents and conditions, as would be recognized by the skilled person, for the introduction of the various moieties found in the formulae as provided herein. For example, the compounds described herein can be modified using various electrophiles or nucleophiles to form new functional groups or substituents.

In one aspect, provided is a compound having a structure of formula (A):

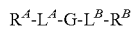  (A), wherein
each of $R^A$ and $R^B$ is independently a radical comprising an oxaborole moiety;
each of $L^A$ and $L^B$ is independently —O— or

each of R and R' is independently hydrogen, unsubstituted or substituted $C_{1-18}$-alkyl, arylalkyl, aryl, or heterocyclic moiety; and
G is a substituted or unsubstituted $C_{1-18}$-alkylene, arylalkylene, arylene, or heterocyclic moiety; and agriculturally acceptable salts thereof.

In one embodiment, the volatile compound is an antimicrobial compound. In another embodiment, the volatile compound has use against pathogens affecting meats, plants, or plant parts, comprising contacting the meats, plants, or plant parts. In another embodiment, the -$L^A$-G-$L^B$- portion of formula (A) is derived from a diol or diamine compound. In a further embodiment, the diol compound is selected from the group consisting of 1,2-ethylene glycol; 1,2-propylene glycol; 1,3-propylene glycol; 1,1,2,2-tetramethyl-1,2-ethylene glycol; 2,2-dimethyl-1,3-propylene glycol; 1,6-hexanediol; 1,10-decanediol; and combinations thereof. In another embodiment, the diamine compound is 1,2-ethylene diamine; 1,3-propylene diamine; or combinations thereof. In another embodiment, $L^A$ and $L^B$ are identical. In another embodiment, $L^A$ and $L^B$ are different. In another embodiment, each of $L^A$ and $L^B$ is independently —O— or —NH—. In another embodiment, $L^A$ and $L^B$ are identical. In another embodiment, $L^A$ and $L^B$ are different.

In another embodiment, the -$L^A$-G-$L^B$- portion of formula (A) comprises asymmetrical functional groups (i.e., asymmetrical bridges). In a further embodiment, the -$L^A$-G-$L^B$- portion of formula (A) comprises one hydroxyl group and one amine group. In a further embodiment, the -$L^A$-G-$L^B$- portion of formula (A) comprises an amino alcohol. In another embodiment, G is a substituted or unsubstituted $C_{1-8}$-alkylene. In a further embodiment, G is a substituted or unsubstituted $C_{1-4}$-alkylene. In a further embodiment, G is selected from —$CH_2$—, —$CH_2$—$CH_2$—, and —$CH_2$—$CH_2$—$CH_2$—.

In another embodiment, each of $R^A$ and $R^B$ is independently derived from a member selected from the group consisting of 5-fluoro-1,3-dihydro-1-hydroxy-2,1-benzoxaborole; 5-chloro-1,3-dihydro-1-hydroxy-2,1-benzoxaborole; 1,3-dihydro-1-hydroxy-2,1-benzoxaborole; and combinations thereof. In another embodiment, $R^A$ and $R^B$ are identical. In another embodiment, $R^A$ and $R^B$ are different.

In another embodiment, at least one of $R^A$ and $R^B$ is selected from formula (B), (C), or (D):

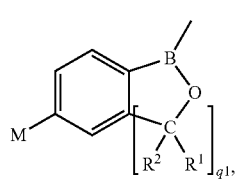

(B)

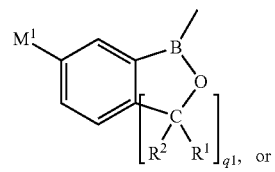

(C)

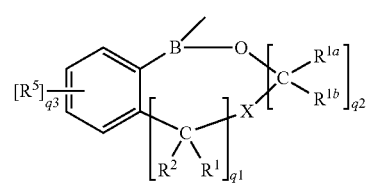

(D)

wherein q1 and q2 are independently 1, 2, or 3;
q3=0, 1, 2, 3, or 4;
B is boron;
M is hydrogen, halogen, —$OCH_3$, or —$CH_2$—O—$CH_2$—O—$CH_3$;
$M^1$ is halogen, —$CH_2OH$, or —$OCH_3$;
X is O, S, or $NR^{1c}$, wherein $R^{1c}$ is hydrogen, substituted alkyl, or unsubstituted alkyl;
$R^1$, $R^{1a}$, $R^{1b}$, $R^2$, and $R^5$ are independently hydrogen, OH, $NH_2$, SH, CN, $NO_2$, $SO_2$, $OSO_2OH$, $OSO_2NH_2$, substituted or unsubstituted cycloalkyl, substituted or unsubstituted heterocycloalkyl, substituted or unsubstituted aryl, or substituted or unsubstituted heteroaryl;
and agriculturally acceptable salts thereof.

Additional oxaborole moieties are also disclosed previously in U.S. Pat. No. 8,106,031, and International Patent Application WO 2007/131072A2, the contents of which are hereby incorporated by reference in their entireties.

In another embodiment, at least one of $R^A$ and $R^B$ has a structure of formula (F):

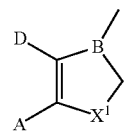

(F)

wherein A and D together with the carbon atoms to which they are attached form a 5, 6, or 7-membered fused ring which may be substituted by $C_{1-6}$-alkyl, $C_{1-6}$-alkoxy, hydroxy, halogen, nitro, nitrile, amino, amino substituted by one or more $C_{1-6}$-alkyl groups, carboxy, acyl, aryloxy, carbonamido, carbonamido substituted by $C_{1-6}$-alkyl, sulphonamido or trifluoromethyl or the fused ring may link two oxaborole rings; B is boron;
$X^1$ is a group —$CR^7R^8$ wherein $R^7$ and $R^8$ are each independently hydrogen, $C_{1-6}$-alkyl, nitrile, nitro, aryl, aralkyl or $R^7$ and $R^8$ together with the carbon atom to which they are attached form an alicyclic ring; and
and agriculturally acceptable salts thereof.

Additional oxaborole moieties are also disclosed previously in U.S. Pat. No. 5,880,188, the content of which is hereby incorporated by reference in its entirety.

In another embodiment, at least one of $R^A$ and $R^B$ is selected from formula (E) or (G):

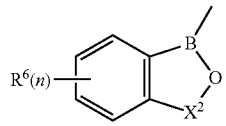
(E)

wherein each $R^6$ is independently hydrogen, alkyl, alkene, alkyne, haloalkyl, haloalkene, haloalkyne, alkoxy, alkeneoxy, haloalkoxy, aryl, heteroaryl, arylalkyl, arylalkene, arylalkyne, heteroarylalkyl, heteroarylalkene, heteroarylalkyne, halogen, hydroxyl, nitrile, amine, ester, carboxylic acid, ketone, alcohol, sufide, sulfoxide, sulfone, sulfoximine, sulfilimine, sulfonamide, sulfate, sulfonate, nitroalkyl, amide, oxime, imine, hydroxylamine, hydrazine, hydrazone, carbamate, thiocarbamate, urea, thiourea, carbonate, aryloxy, or heteroaryloxy;

n=1, 2, 3, or 4;

B is boron;

$X^2=(CR^6{}_2)_m$ where m=1, 2, 3, or 4; or

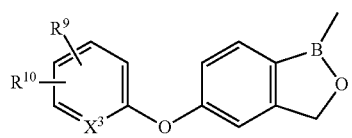
(G)

wherein $R^9$ is CN, $C(O)NR^{11}R^{12}$, or $C(O)OR^3$ wherein $R^3$ is hydrogen, substituted alkyl, or unsubstituted alkyl, $X^3$ is N, CH and $CR^{10}$;

$R^{10}$ is halogen, substituted or unsubstituted alkyl, $C(O)R^{14}$, $C(O)OR^{14}$, $OR^{14}$, $NR^{14}R^{15}$, wherein each of $R^{11}$, $R^{12}$, $R^{14}$, and $R^{15}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

and agriculturally acceptable salts thereof.

In a further embodiment when at least one of $R^A$ and $R^B$ has a structure of formula (G), $R^9$ is CN and $R^{10}$ is $R^b$.

In another embodiment, at least one of $R^A$ and $R^B$ has a structure selected from:

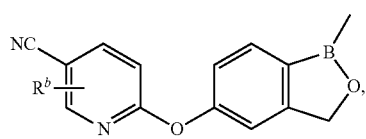

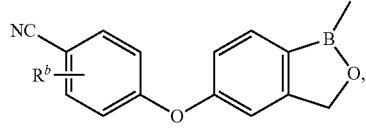

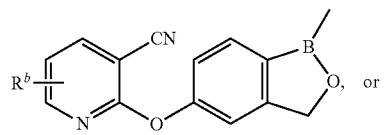
or

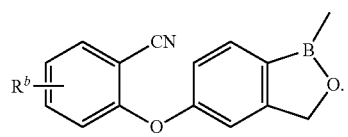

In another embodiment, at least one of $R^A$ and $R^u$ has a structure selected from:

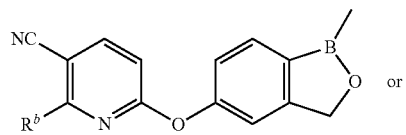
or

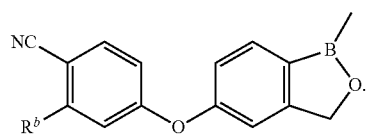

In another embodiment, at least one of $R^A$ and $R^B$ has a structure selected from:

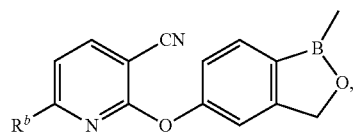

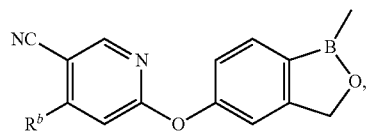

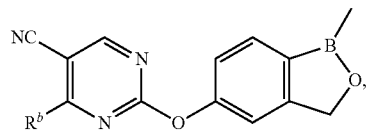

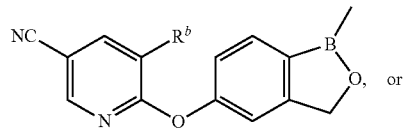
or

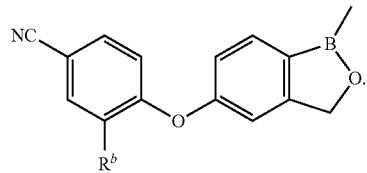

In another embodiment when at least one of $R^A$ and $R^B$ has a structure of formula (G), $R^9$ is —$COOR^3$ and $R^{10}$ is $R^b$.

In another embodiment, at least one of $R^A$ and $R^B$ has a structure selected from:

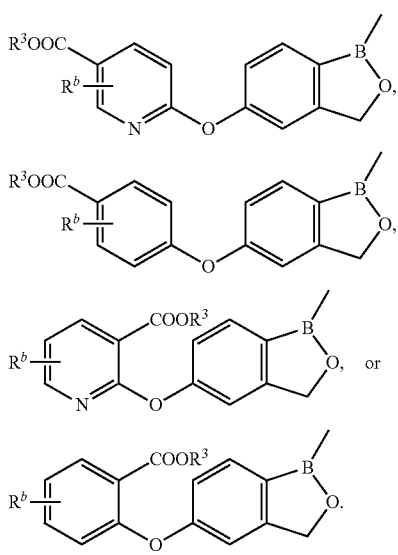

In another embodiment, at least one of $R^A$ and $R^B$ has a structure selected from:

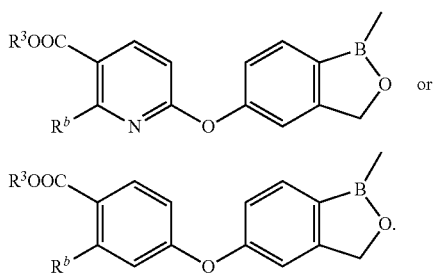

In another embodiment, at least one of $R^A$ and $R^B$ has a structure selected from:

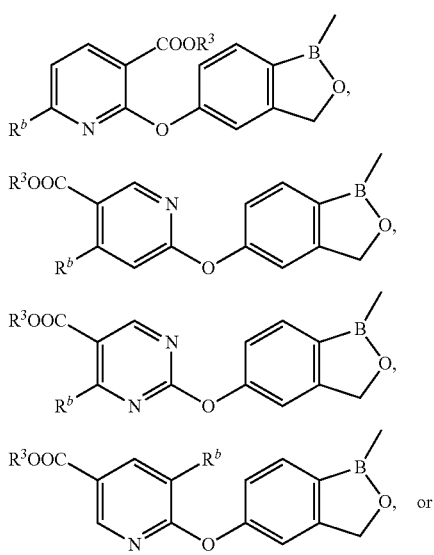

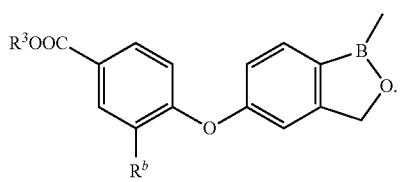

In another embodiment when at least one of $R^A$ and $R^B$ has a structure of formula (G), $R^9$ is —CONR$^1$R$^2$ and $R^{10}$ is $R^b$.

In another embodiment, each of $R^A$ and $R^B$ is independently selected from formula (B), (C), (D), (E), (F), or (G).

In another embodiment, the volatile compound of the invention is selected from:

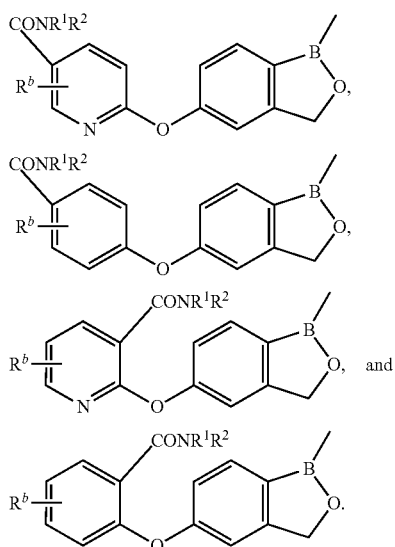

In another embodiment, the volatile compound of the invention is selected from:

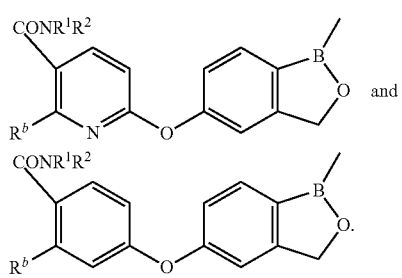

In another embodiment, the volatile compound of the invention is selected from:

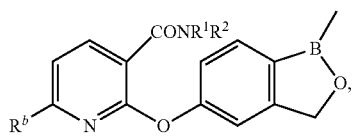

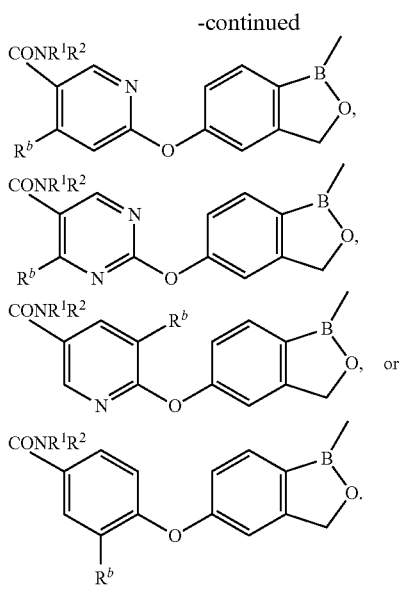

In one embodiment, $R^b$ is selected from fluorine and chlorine. In another embodiment, $R^b$ is selected from $OR^{20}$ and $NR^{21}R^{22}$. In another embodiment when $R^b$ is $OR^{20}$, $R^{20}$ is selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In another embodiment when $R^b$ is $OR^{20}$, $R^{20}$ is selected from H, substituted or unsubstituted alkyl, substituted or unsubstituted heteroalkyl and substituted or unsubstituted cycloalkyl. In another embodiment when $R^b$ is $OR^{20}$, $R^{20}$ is unsubstituted $C_{1-6}$ alkyl. In another embodiment when $R^b$ is $OR^{20}$, $R^{20}$ is unsubstituted cycloalkyl. In another embodiment when $R^b$ is $OR^{20}$, $R^{20}$ is alkyl, substituted with a member selected from substituted or unsubstituted $C_{1-6}$ alkoxy. In another embodiment when $R^b$ is $OR^{20}$, $R^{20}$ is alkyl, substituted with at least one halogen. In another embodiment when $R^b$ $OR^{20}$, $R^{20}$ is alkyl, substituted with at least one oxo moiety.

In another embodiment when $R^b$ is $OR^{20}$, $R^{20}$ is a member selected from —$CH_3$, —$CH_2CH_3$, —$(CH_2)_2CH_3$, —$CH(CH_3)_2$, —$CH_2CF_3$, —$CH_2CHF_2$, —$CH_2CH_2(OH)$, —$CH_2CH_2(OCH_3)$, —$CH_2CH_2(OC(CH_3)_2)$, —$C(O)CH_3$, —$CH_2CH_2OC(O)CH_3$, —$CH_2C(O)OCH_2CH_3$, —$CH_2C(O)OC(CH_3)_3$, —$(CH2)_3C(O)CH_3$, —$CH_2C(O)OC(CH_3)_3$, cyclopentyl, cyclohexyl,

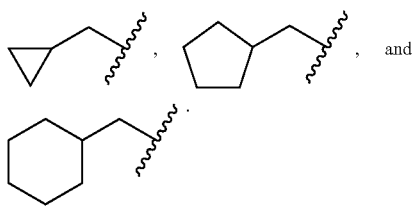

In another embodiment when $R^b$ is $NR^{21}R^{22}$, $R^{21}$ and $R^{22}$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In another embodiment when $R^b$ is $NR^{21}R^{22}$, $R^{21}$ is H or unsubstituted alkyl; and $R^{22}$ is unsubstituted alkyl or alkyl substituted with a member selected from hydroxyl, phenyl, unsubstituted alkoxy and alkoxy substituted with a phenyl. In a further embodiment when $R^b$ is $NR^{21}R^{22}$, $R^{21}$ is H or $CH_3$.

In another embodiment when $R^b$ is $NR^{21}R^{22}$, $R^{21}$ and $R^{22}$ are independently selected from substituted or unsubstituted alkyl. In another embodiment when $R^b$ is $NR^{21}R^{22}$, $R^{21}$ is unsubstituted alkyl; and $R^2$ is substituted or unsubstituted alkyl. In another embodiment when $R^b$ is $NR^{21}R^{22}$, $R^{21}$ is unsubstituted alkyl; and $R^{22}$ is alkyl, substituted with a member selected from substituted or unsubstituted alkoxy and hydroxyl. In another embodiment when $R^b$ is $NR^{21}R^{22}$, $R^{21}$ is unsubstituted alkyl; and $R^{22}$ is alkyl, substituted with unsubstituted alkoxy. In another embodiment when $R^b$ is $NR^{21}R^{22}$, $R^{21}$ is unsubstituted alkyl; and $R^{22}$ is alkyl, substituted with alkoxy, substituted with phenyl. In another embodiment when $R^b$ is $NR^{21}R^{22}$, $R^{21}$ is unsubstituted alkyl; and $R^{22}$ is alkyl, substituted with unsubstituted alkoxy. In another embodiment when $R^b$ is $NR^{21}R^{22}$, $R^{21}$ and $R^{22}$ together with the nitrogen to which they are attached, are combined to form a 4- to 8-membered substituted or unsubstituted heterocycloalkyl ring. In another embodiment when $R^b$ is $NR^{21}R^{22}$, $R^{21}$ and $R^{22}$ together with the nitrogen to which they are attached, are combined to form a 5- or 6-membered substituted or unsubstituted heterocycloalkyl ring.

In another embodiment, $R^b$ is selected from $N(CH_3)_2$, $N(CH_3)(CH_2CH_2(OCH_3))$, $N(CH_3)(CH_2CH_2OH)$, $NH_2$, $NHCH_3$, $NH(CH_2CH_2(OCH_3))$, $NH(CH_2CH_2(OCH_2Ph))$, $NH(CH_2Ph)$, $NH(C(CH_3)_3)$ and $NH(CH_2CH_2OH)$. In another embodiment, $R^b$ is selected from

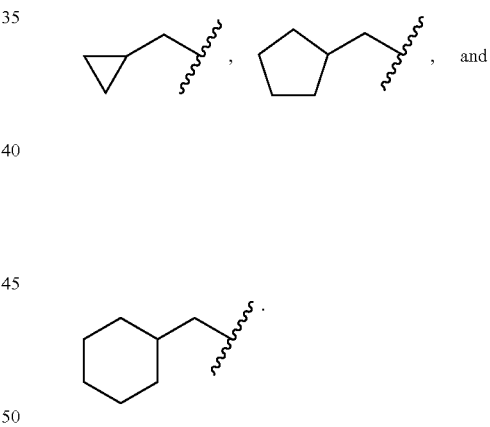

Additional oxaborole moieties are also disclosed previously in U.S. Pat. No. 8,039,450, and patent application publication US 2009/0291917, the contents of which are hereby incorporated by reference in their entireties.

In another embodiment, the compound provided has a structure of formula (A1) or (A2):

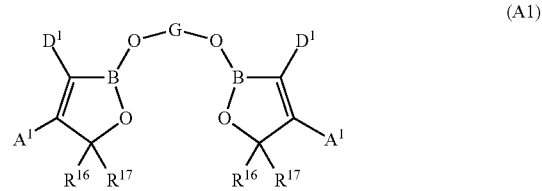

(A1)

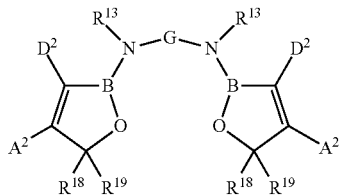

(A2)

wherein each of $A^1$, $A^2$, $D^1$, and $D^2$ is independently hydrogen, substituted or unsubstituted $C_{1-18}$-alkyl, arylalkyl, aryl, or heterocyclic; or $A^1$ and $D^1$, or $A^2$ and $D^2$ together form a 5, 6, or 7-membered fused ring which is substituted or unsubstituted;

each of $R^{13}$, $R^{16}$, $R^{17}$, $R^{18}$, and $R^{19}$ is independently hydrogen, substituted or unsubstituted $C_{1-6}$-alkyl, nitrile, nitro, aryl or aryl alkyl; or $R^{16}$ and $R^{17}$, or $R^{18}$ and $R^{19}$ together form an alicyclic ring which is substituted or unsubstituted;

B is boron; and

G is a substituted or unsubstituted $C_{1-18}$-alkylene, arylalkylene, arylene, or heterocyclic moiety.

In another embodiment, each of $R^A$ and $R^B$ is independently

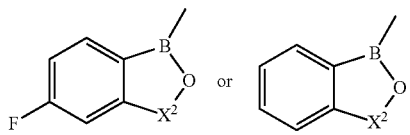

wherein $X^2 = (CR^6_2)_m$ and m=1, 2, 3, or 4.

In another embodiment, each of $R^A$ and $R^B$ is independently

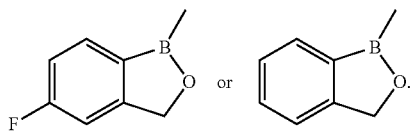

In another embodiment, the compound provided has the structure of

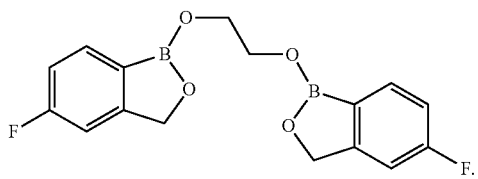 [SMILES: Fc1ccc2c(c1)COB2OCCOB1OCc2cc(F)ccc21]

Meats, plants, or plant parts may be treated in the practice of the present invention. One example is treatment of whole plants; another example is treatment of whole plants while they are planted in soil, prior to the harvesting of useful plant parts.

Any plants that provide useful plant parts may be treated in the practice of the present invention. Examples include plants that provide flowers, fruits, vegetables, and grains.

As used herein, the phrase "plant" includes dicotyledonous plants and monocotyledonous plants. Examples of dicotyledonous plants include tobacco, *Arabidopsis*, soybean, tomato, papaya, canola, sunflower, cotton, alfalfa, potato, grapevine, pigeon pea, pea, *Brassica*, chickpea, sugar beet, rapeseed, watermelon, melon, pepper, peanut, pumpkin, radish, spinach, squash, broccoli, cabbage, carrot, cauliflower, celery, Chinese cabbage, cucumber, eggplant, and lettuce. Examples of monocotyledonous plants include corn, rice, wheat, sugarcane, barley, rye, sorghum, orchids, bamboo, banana, cattails, lilies, oat, onion, millet, and triticale. Examples of fruit include banana, pineapple, oranges, grapes, grapefruit, watermelon, melon, apples, peaches, pears, kiwifruit, mango, nectarines, guava, persimmon, avocado, lemon, fig, and berries. Examples of flowers include baby's breath, carnation, dahlia, daffodil, geranium, gerbera, lily, orchid, peony, Queen Anne's lace, rose, snapdragon, or other cut-flowers or ornamental flowers, potted-flowers, and flower bulbs.

The present application also provides methods of preparing a compound. One method embodiment comprises:

(a) mixing at least one oxaborole compound with at least one adducting compound in a first organic solvent; and (b) evaporating the first organic solvent by heating, thereby allowing the at least one adducting compound to react with the at least one oxaborole compound to generate at least one adducted product.

In another embodiment, the heating is performed at a temperature between 110° C. and 125° C.; between 100° C. and 150° C.; or between 80° C. and 200° C.

In another embodiment, the at least one adducting compound comprises a diol or diamine compound. In a further embodiment, the diol compound is selected from the group consisting of 1,2-ethylene glycol; 1,2-propylene glycol; 1,3-propylene glycol; 1,1,2,2-tetramethyl-1,2-ethylene glycol; 2,2-dimethyl-1,3-propylene glycol; 1,6-hexanediol; 1,10-decanediol; and combinations thereof. In another embodiment, the diamine compound is 1,2-ethylene diamine; 1,3-propylene diamine; or combinations thereof.

In another embodiment, step (a) further includes mixing at least one catalyst with the at least one oxaborole compound and at least one adducting compound. In a further embodiment, the catalyst is selected from the group consisting of amine, phosphine, heterocyclic nitrogen, ammonium, phosphonium, arsonium, sulfonium moieties, and combinations thereof. In another embodiment, the catalyst is selected from the group consisting of a phosphonium compound, an ammonium compound, chromium salts, amino compounds and combinations thereof. In another embodiment, the catalyst is selected from the group consisting of 2-methyl imidazole, 2-phenyl imidazole, an imidazole derivative, 1,8-diazabicyclo[5.4.0]undec-7-ene (DBU), and combinations thereof.

Those skilled in the art would understand certain variation can exist based on the disclosure provided. Thus, the following examples are given for the purpose of illustrating the invention and shall not be construed as being a limitation on the scope of the invention or claims.

EXAMPLES

Example 1

Preparation of Sample 1

3.20 g of 5-fluoro-1,3-dihydro-1-hydroxy-2,1-benzoxaborole (21.2 mmol) and 3.20 g of ethylene glycol (51.6 mmol) are heated in 40 g of toluene. The toluene water azeotrope is distilled out of the system until the head temperature reached 110° C. The toluene is removed via rotary evaporator and the excess ethylene glycol is removed by kugelrohr distillation at about 20 torr and 100° C. bath temperature. Recrystallization from toluene generates 2.95 g of white crystals, mp 145-149° C. Proton nmr shows spectra and integration consistent with the two to one product below:

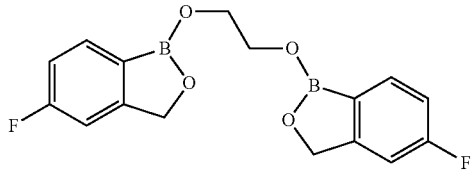 [SMILES: Fc1ccc2c(c1)COB2OCCOB1OCc2cc(F)ccc21]

Example 2

Preparation of Sample 2

3.00 g of 1,3-dihydro-1-hydroxy-2,1-benzoxaborole (22.4 mmol) and 3.00 g of ethylene glycol (46.9 mmol) are heated in 40 g of toluene. The toluene water azeotrope is distilled out of the system until the head temperature reached 110° C. The toluene is removed via rotary evaporator and the excess ethylene glycol is removed by kugelrohr distillation at about 20 torr and 100° C. bath temperature. Recrystallization from toluene generates 2.49 g of white crystals, mp 118-120.5° C. Proton NMR shows spectra and integration consistent with the two to one product.

Example 3

Preparation of Sample 3

3.17 g of 5-fluoro-1,3-dihydro-1-hydroxy-2,1-benzoxaborole (21.0 mmol) and 3.22 g of pinacol (27.3 mmol) are heated in 40 g of toluene. The toluene water azeotrope is distilled out of the system until the head temperature reached 110° C. The toluene is removed via rotary evaporator and the excess pinacol is removed by kugelrohr distillation at about 20 torr and 120° C. bath temperature. Recrystallization from hexane generates 3.21 g of white crystals, mp 81-89° C. Proton NMR shows spectra and integration consistent with the two to one product.

Example 4

Preparation of Sample 4

3.0 g of 5-fluoro-1,3-dihydro-1-hydroxy-2,1-benzoxaborole (19.9 mmol) and 2.5 g of 1,2-propanediol (propylene glycol; 32.9 mmol) are heated in 40 g of toluene. The toluene water azeotrope is distilled out of the system until the head temperature reached 110° C. The toluene is removed via rotary evaporator and the excess propylene glycol is removed by kugelrohr distillation at about 20 torr and 110° C. bath temperature. Recrystallization from hexane generates 3.49 g of white crystals, mp 65.5-68.5° C. Proton NMR shows spectra and integration consistent with the two to one product.

Example 5

In Vitro Analysis 12-well (6.5 ml volume per well) microtiter plates are used for the in vitro inhibition assay for volatile antimicrobial compounds. A 3-ml volume of full-strength Potato Dextrose Agar (PDA) is added to each well. After cooling, 1 μL of $1 \times 10^5$ spores per ml Botrytis cinerea (ATCC #204446) spore suspension is spot pipetted to the agar in the centre of the well.

TABLE 1

Antimicrobial activities of Samples 1-4 (50 μl/disk)

| | MIC mg/l | | | | |
|---|---|---|---|---|---|
| ID | Botrytis cinerea | Penicillium expansum | Alternaria alternata | Monilinia fructicola | Glomerella cingulata |
| Sample 1 | <0.6 | 8.9 | 2.2 | — | — |
| Sample 2 | <0.6 | 8.9 | 8.9 | 35.7 | 142.9 |
| Sample 3 | <0.6 | 4.5 | 2.2 | — | — |
| Sample 4 | <0.6 | 8.9 | 1.1 | — | — |

Whatman #1 filter disks (1.5 cm; Cat. No. 1001-0155) are placed on the underside of a polyethylene PCR plate sealing film. For determination of the minimum inhibitory concentration (MIC), test compounds are diluted in acetone, in duplicate, and 50 μl of the compound solution is added to disks at concentrations that can vary from 0.001 mg/l to 1142.9 mg/l.

The acetone is permitted to evaporate for 5 minutes. The headspace around the Botrytis cinerea inoculum is then sealed inside the well by the film with the adhering disk containing the fungicide. Plates are inverted to prevent any possibility of the chemical from flaking from the disk and falling onto the inoculated agar. After 3 days of incubation at 23° C., cultures are evaluated for percent growth relative to control and determination of MIC. Samples 1-4 show good antimicrobial activity against Botrytis cinerea and/or other pathogens in this in vitro analysis. Minimum inhibitory concentrations (MIC) are shown in Tables 1 and 2 for results from two separate tests.

TABLE 2

Antimicrobial activities of Samples 1-4 (repeat test; 50 μl/disk)

| | MIC mg/l | | | | |
|---|---|---|---|---|---|
| ID | Botrytis cinerea | Penicillium expansum | Alternaria alternata | Monilinia fructicola | Glomerella cingulata |
| Sample 1 | 0.6 | 8.9 | >2.2 | 2.2 | — |
| Sample 2 | 2.2 | 8.9 | — | — | — |
| Sample 3 | 1.1 | 8.9 | >2.2 | 1.1 | — |
| Sample 4 | 0.6 | 8.9 | >2.2 | 1.1 | — |

Example 6

Grape In Vivo Analysis

In order to assess the in vivo activity of volatile antimicrobial compounds, a volatile bioassay is developed using green table grape. Fruit are removed from the rachis, and 16 to 20 fruit are placed inside a 1 dry pint clamshell (Produce Packaging; Product #03231004KZ) with the stem wound facing upwards. The grapes are inoculated by pipetting 20 μL of $1 \times 10^6$ spore per ml Botrytis cinerea (ATCC #204446) into the stem wound. The clamshell is placed inside a 2.55 L plastic container (Snapware; Model #1098421). A Whatman #1 filter paper (4.25 cm; Cat. No. 1001-042) is placed on a watchglass, which is then placed on top of the closed clamshell lid. For determination of the MIC, test compounds are diluted in acetone, and 400 μl of the solution is added to disks, in duplicate, in a dose dependent manner (for example 0.4 to 50 mg/liter). The acetone is permitted to evaporate for 5 minutes. The plastic containers are then closed and placed for 3 days at 21° C. Clamshells are then removed from the treatment plastic container and placed into separate larger secondary containers for a further 3 days of evaluation at 21° C. During these 3 days, fruit are evaluated daily for incidence and severity of disease and symptoms of phytotoxicity. Samples 1-4 show good antimicrobial activity against *Botrytis cinerea* in this in vivo analysis and no phytotoxicity.

Example 7

Strawberry In Vivo Analysis

In order to assess the in vivo activity of volatile antimicrobial compounds, a volatile bioassay is developed using strawberry. Fruit (6 to 8) are placed inside a 1 lb clamshell (Packaging Direct Inc.; Product #4341699) with the calyx facing downward. The strawberry fruit are wound-inoculated by pipetting 20 μL of 1×10⁶ spore per ml *Botrytis cinerea* (ATCC #204446) into a wound approximately 5 mm deep and 2.6 mm in width. The clamshell is placed inside a 2.55 L plastic container (Snapware; Model #1098421). A Whatman #1 filter paper (4.25 cm; Cat. No. 1001-042) is placed on a watchglass, which is then placed on top of the closed clamshell lid. For determination of the MIC, test compounds are diluted in acetone, and 400 μl of the solution is added to disks, in duplicate, in a dose dependent manner (for example 0.4 to 50 mg/liter). The acetone is permitted to evaporate for 5 minutes. The plastic containers are then closed and placed for 3 days at 21° C. Clamshells are then removed from the treatment plastic container and placed into separate larger secondary containers for a further 3 days of evaluation at 21° C. During these 3 days, fruit are evaluated daily for incidence and severity of disease and symptoms of phytotoxicity. Samples 1-4 show good antimicrobial activity against *Botrytis cinerea* in this in vivo analysis and no phytotoxicity.

Example 8

Antimicrobial Activity Against Bacteria 12-well (6.5 ml volume per well) microtiter plates are used for the in vitro inhibition assay for volatile antimicrobial compounds. A 3-ml volume of full-strength LB Agar is added to each well. After cooling, 15 μL of *Escherichia coli* (ATCC #25922) adjusted to an optical density of 0.02 to 0.035, and further diluted 1/10 is pipetted to the centre of the agar. The plate is tilted to distribute bacteria uniformly. Whatman #1 filter disks (1.5 cm; Cat. No. 1001-0155) are placed on the underside of a polyethylene PCR plate sealing film. For determination of the minimum inhibitory concentration (MIC), test compounds are diluted in acetone, in duplicate, and 50 μl of compound is added to disks at concentrations that can vary from 0.015 to 35.7 mg/l. The acetone is permitted to evaporate for 5 minutes. The headspace around the *Escherichia coli* inoculum is then sealed inside the well by the film with the adhering disk containing the fungicide. Plates are inverted, placed over the treated disks and sealed to prevent any of the chemical from flaking from the disk and falling onto the inoculated agar. After 2 days of incubation at 23° C., cultures were evaluated for colony growth relative to control. Samples 1-4 show good antimicrobial activity against *Escherichia coli* in this in vitro analysis.

We claim:

1. A method of using a compound against pathogens affecting meats, plants, or plant parts, comprising contacting the meats, plants, or plant parts with an effective amount of a compound having a structure of formula (A):

$$R^A\text{-}L^A\text{-}G\text{-}L^B\text{-}R^B \quad (A)$$

wherein each of $R^A$ and $R^B$ is independently an oxaborole moiety;

each of $L^A$ and $L^B$ is independently —O—,

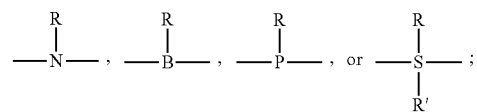

each of R and R' is independently hydrogen, unsubstituted or substituted $C_{1-18}$-alkyl, arylalkyl, aryl, or heterocyclic moiety; and G is a substituted or unsubstituted $C_{1-18}$-alkylene, arylalkylene, arylene, or heterocyclic moiety;

and agriculturally acceptable salts thereof.

2. The method of claim 1, wherein each of $R^A$ and $R^B$ is independently derived from a member selected from the group consisting of 5-fluoro-1,3-dihydro-1-hydroxy-2,1-benzoxaborole; 5-chloro-1,3-dihydro-1-hydroxy-2,1-benzoxaborole; 1,3-dihydro-1-hydroxy-2,1-benzoxaborole; and combinations thereof;

the -$L^A$-G-$L^B$- portion of formula (A) is derived from a diol or diamine compound; the diol compound is selected from the group consisting of 1,2-ethylene glycol; 1,2-propylene glycol; 1,3-propylene glycol; 1,1,2,2-tetramethyl-1,2-ethylene glycol; 2,2-dimethyl-1,3-propylene glycol; 1,6-hexanediol; 1,10-decanediol; and combinations thereof; and the diamine compound is 1,2-ethylene diamine; 1,3-propylene diamine; or combinations thereof;

G is a substituted or unsubstituted $C_{1-8}$-alkylene;

and agriculturally acceptable salts thereof.

3. The method of claim 1, wherein the compound is volatile.

4. The method of claim 1, wherein the compound is a fungicide.

5. The method of claim 1, wherein G is selected from —$CH_2$—, —$CH_2$—$CH_2$—, —$CH_2$—$CH_2$—$CH_2$—, —CH($CH_3$)—$CH_2$—, —C($CH_3$)$_2$—C($CH_3$)$_2$, and —$CH_2$—C($CH_3$)$_2$—$CH_2$—.

6. The method of claim 1, wherein each of $R^A$ and $R^B$ is independently

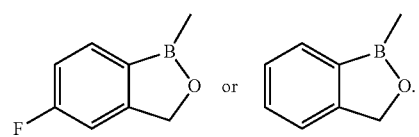

7. The method of claim 1, wherein the compound has the structure of

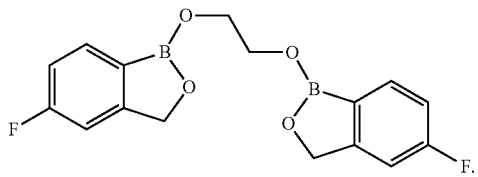 [SMILES: Fc1ccc2c(c1)COB2OCCOB1OCc2cc(F)ccc21]

8. The method of claim 1, wherein the meats, plants, or plant parts are selected from the group consisting of barley, camphor tree, canola, castor-oil plant, cinnamon, cocoa, coffee, corn, cotton, flax, grapevine, hemp, hops, jute, maize, mustard, nuts, oat, poppy, rape, rice, rubber plant, rye, sunflower, sorghum, soybean, sugar cane, tea, tobacco, and wheat.

9. The method of claim 1, wherein the plants are selected from the group consisting of banana, pineapple, citrus, grapes, watermelon, cantaloupe, muskmelon, and other melons, apple, peach, pear, cherry, kiwifruit, mango, nectarine, guava, papaya, persimmon, pomegranate, avocado, fig, citrus, and berries.

10. The method of claim 1, wherein the compound has a structure of formula (A1) or (A2):

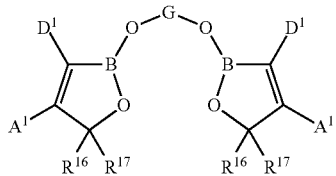

(A1)

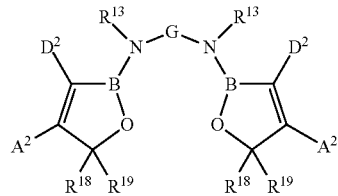

(A2)

wherein each of $A^1$, $A^2$, $D^1$, and $D^2$ is independently hydrogen, substituted or unsubstituted $C_{1-18}$-alkyl, arylalkyl, aryl, or heterocyclic; or $A^1$ and $D^1$, or $A^2$ and $D^2$ together form a 5, 6, or 7-membered fused ring which is substituted or unsubstituted;

each of $R^{16}$, $R^{17}$, $R^{18}$, and $R^{19}$ is independently hydrogen, substituted or unsubstituted $C_{1-6}$-alkyl, nitrile, nitro, aryl or aryl alkyl; or $R^{16}$ and $R^{17}$, or $R^{18}$ and $R^{19}$ together form an alicyclic ring which is substituted or unsubstituted;

B is boron; and

G is a substituted or unsubstituted $C_{1-18}$-alkylene, arylalkylene, arylene, or heterocyclic moiety;

and agriculturally acceptable salts thereof.

11. The method of claim 1, wherein each of $R^A$ and $R^B$ is independently derived from the group consisting of 5-fluoro-1,3-dihydro-1-hydroxy-2,1-benzoxaborole; 5-chloro-1,3-dihydro-1-hydroxy-2,1-benzoxaborole; 1,3-dihydro-1-hydroxy-2,1-benzoxaborole; and combinations thereof.

12. The method of claim 1, wherein the -$L^A$-G-$L^B$- portion of formula (A) is derived from a diol or diamine compound.

13. The method of claim 12, wherein the diol compound is selected from the group consisting of 1,2-ethylene glycol; 1,2-propylene glycol; 1,3-propylene glycol; 1,1,2,2-tetramethyl-1,2-ethylene glycol; 2,2-dimethyl-1,3-propylene glycol; 1,6-hexanediol; 1,10-decanediol; and combinations thereof.

14. The method of claim 12, wherein the diamine compound is 1,2-ethylene diamine; 1,3-propylene diamine; or combinations thereof.

* * * * *